United States Patent [19]

Drewlow

[11] Patent Number: Plant 6,434

[45] Date of Patent: Nov. 29, 1988

[54] BEGONIA PLANT NAMED CHANTILLY

[75] Inventor: Lyndon W. Drewlow, Ashtabula, Ohio

[73] Assignee: Mikkelsens, Inc., Ashtabula, Ohio

[21] Appl. No.: 20,761

[22] Filed: Mar. 2, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Begonia plant named Chantilly, characterized by its rose pink flower color; ruffled, double flowers with petals slightly cut at margins; strong stems and very upright growth habit with good branching; early and profuse flowering, and excellent flower retention during shipping.

1 Drawing Sheet

1

The present invention relates to a new and distinctive cultivar of Begonia plant, botanically known as *Begonia hiemalis,* Fotsch, and known by the cultivar name Chantilly.

The new cultivar was discovered by me as a seedling from a controlled crossing of *B. tuberhybrida,* Mikkelsen Seedling No. 84-613-5, as the seed parent with *B. socotrana,* Mikkelsen Seedling No. 84-1019-6, as the pollen parent.

Asexual reproduction by stem and/or leaf cuttings by me at Ashtabula, Ohio, has reproduced the unique features of the new cultivar through successive propagations.

The following characteristics distinguish Chantilly from both its parents and other begonias commercially known and used in the floriculture industry. In describing the characteristics, reference has been made to other cultivars, including Barbara (U.S. Plant Pat. No. 5,179), Aphrodite Pink (U.S. Plant Pat. No. 3,318), Imke (U.S. Plant Pat. No. 5,539), and Greta and Taffeta, both of which are not patented.

1. Chantilly is a rose-pink flowered cultivar. Both Barbara and Aprodite Pink have lighter pink flowers; Greta is more salmon colored, Imke is rose-red, and Taffeta is salmon-red in color.

2. Chantilly has a ruffled flower with petals slightly cut at the margins; Aphrodite Pink and Greta have ruffled petals but margins are not cut, while Taffeta, Barbara and Imke have a non-ruffled flower.

3. Flower size of Chantilly is equal to Aphrodite Pink and Greta but larger than Imke, Barbara & Taffeta. The flower form of Chantilly is more double than Aphrodite Pink, and similar in doubleness to the others.

4. Chantilly has a cyme inflorescence which is similar to Taffeta and Greta, while Aphrodite Pink, Imke and Barbara have a raceme type inflorescence.

5. Chantilly has strong stems and is a very upright grower similar to Barbara and Imke; Aphrodite Pink, Greta and Taffeta have weaker stems that tend to bend when several flowers are open.

6. Chantilly is similar in height to Aphrodite Pink and taller than the other four comparison cultivars.

7. Leaf size is similar to Barbara and Aphrodite Pink, while Taffeta, Greta and Imke have smaller leaves.

8. Leaf color is similar to Imke and Greta, with Aphrodite Pink and Barbara having lighter green leaves and Taffeta a more yellow green leaf with a red tinge.

9. Underside of immature leaf of Chantilly has a red margin with a touch of red in rest of leaf, while Barbara

2 has a red margin with green leaf area, Imke a tough of red on leaf but no red margins, Aphrodite Pink more red on leaf area, Greta is intermediate for red, and Taffeta is deep maroon red on underside except for veins.

10. Chantilly has a fringed appearance due to cut on margin and ruffled form.

11. Easy to propagate, both from stem and leaf cuttings.

12. Branches well from base after a stem cutting is pinched.

13. Early flowering nature.

14. Flowers remain on plant during shipping.

The accompanying colored photograph illustrates in perspective view the overall appearance of Chantilly, showing the colors as true as it is reasonably possible to obtain in a colored reproduction of this type.

The following is a detailed description of my new Begonia cultivar based on plants produced under commercial practices in Ashtabula, Ohio, under greenhouse conditions. The photograph was taken in early June, 1986, and color references are made to the Royal Horticultural Society Colour Chart except where general color terms of ordinary dictionary significance are used.

Parentage:

A controlled cross between *B. tuberhybrida,* Mikkelsen Seedling No. 84-613-5×*B. socotrana,* Mikkelsen Seedling No. 84-1019-6.

Propagation:

(A) *Type cutting.*—Leaf.

(B) *Time to root.*—18 days at 21° C. summer; 21 days at 21° C. winter.

(C) *Rooting habit.*—Fibrous, fine, abundant.

(D) *Time for shoot development.*—10 weeks in summer to 13 weeks in winter to obtain shoots 4 to 5 cm long.

Plant description:

(A) *Form.*—Upright, very strong stems for self-support; semi-compact with intermediate internodes; best for 15 and 25 cm pot production; well branched with green leaves.

(B) *Habit of growth.*—Early, fast, upright growth with excellent branching from base of plant when pinched. Usually vegetative shoots are formed at the basal nodes and flower shoots at the higher nodes.

(C) *Foliage.*—Simple leaves; alternate, borne on strong petioles 7–8 mm in diameter on mature basal leaves. Petioles are green with pinkish tint. (1) Size: 11 to 12 cm across and 13 to 14 cm long on mature basal leaves. Leaf size can vary greatly due to environment, position on plant and number of shoots per plant. (2) Shape: Inequilateral. (3) Texture: Glabrous, leathery. (4) Margin: Doubly serrated. (5) Color: Young foliage, top side 146B; with red tinge in margin; Young foliage, under side 146C; reddish areas on leaf except veins. Mature foliage, top side 147A with areas of 147B; Mature foliage, under side 148C. (6) Venation: Palmate, 5 to 6 major veins.

Flowering description:

(A) *Flowering habits.*—Flowering in cymes with an average of 5 to 6 flowers per cyme. Several cymes are in bloom at one time, and flowering continues more or less indefinitely.

(B) *Natural flowering season.*—Will flower year around without controlling day length. Plants will flower earlier and more abundantly if subjected to a reduced day length of 12 hours.

(C) *Flower buds.*—30 mm wide and 20 mm long just before opening. Tepals are crenated around margins. Color 47C just before opening and 46B when immature.

(D) *Flowers borne.*—On strong upright peduncles; reddish pink in color with the peduncle being 6 mm in diameter. Pedicels are redder in color than the peduncles.

(E) *Quantiy.*—Average of 5 or 6 flowers per peduncle with several open per plant at one time. Flowers open in sequence as the cyme develops.

(F) *Tepals.*—(1) Shape: Almost heart shape and ruffled with cut margins. (2) Color top side in summer when opening: 52B, fading to 54B; underside also 52B, fading to 54B. (3) Number of tepals: 30 or more. (4) Size of tepals: 24 mm long and 28 mm wide. (5) Flower size: First flowers in cyme 60 mm.

(G) *Reproductive organs.*—(1) Stamens: None as plant is full double with anthers appearing as petals. (2) Pistils: None observed to date.

Disease resistance: No insect or disease problems seen to date. Chantilly has shown good disease resistance to powdery mildew.

I claim:

1. A new and distinct cultivar of Begonia plant named Chantilly, as illustrated and described, and particularly characterized by its rose pink flower color, ruffled, double flowers with petals slightly cut at margins; strong stems and very upright growth habit with good branching; early and profuse flowering, and excellent flower retention during shipping.

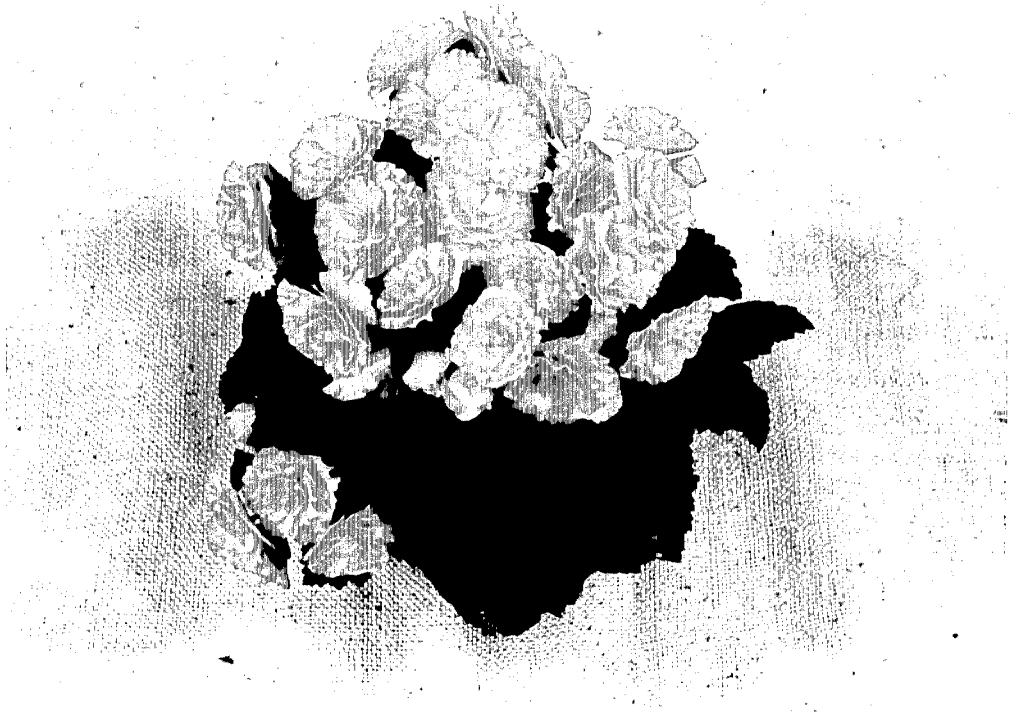

* * * * *